US00PP20895P2

(12) United States Plant Patent
Zerr

(10) Patent No.: US PP20,895 P2
(45) Date of Patent: Mar. 30, 2010

(54) POINSETTIA PLANT NAMED 'FISMIRED'

(50) Latin Name: *Euphorbia pulcherrima*
Varietal Denomination: Fismired

(75) Inventor: Katharina Zerr, Höhr-Grenzhausen (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/321,550

(22) Filed: Jan. 22, 2009

(51) Int. Cl.
*A01H 5/00* (2006.01)

(52) U.S. Cl. ..... Plt./307

(58) Field of Classification Search ..... Plt./307
See application file for complete search history.

*Primary Examiner*—Susan B McCormick Ewoldt
(74) *Attorney, Agent, or Firm*—S. Matthew Edwards

(57) ABSTRACT

A new Poinsettia plant named 'Fismired' particularly distinguished by the brilliant red flower color, distinctly lobed bracts, relatively large inflorescences well above the foliage, dark green, distinctly lobed foliage, well branching, compact plant habit and early flowering.

1 Drawing Sheet

Latin name of the genus and species of the plant claimed: *Euphorbia pulcherrima.*

Varietal denomination: 'Fismired'.

BACKGROUND OF THE NEW PLANT

The present invention comprises a new Poinsettia plant, botanically known as *Euphorbia pulcherrima*, and hereinafter referred to by the variety name 'Fismired.'

'Fismired' is a product of a planned breeding program. The new cultivar 'Fismired' has brilliant red flower color, distinctly lobed bracts and leaves, dark green foliage, early flowering, and compact to medium plant habit.

'Fismired' originated from hybridizations made from late June to early August 2002 in a controlled breeding program in Hillscheid, Germany. The female parent was the commercial variety 'Fiselfi,' U.S. Plant Pat. No. 13,736, with red, distinctly lobed bracts, dark green foliage, and compact habit.

The male parent of 'Fismired' was the proprietary variety 'Fispoin 7776,' unpatented, characterized by deep red bracts, dark green foliage, and about medium sized plant habit.

The resulting seeds were sown in February to March 2003. 'Fismired' was selected as one flowering plant within the progeny of the stated cross in December 2003 in a controlled environment in Hillscheid, Germany.

The first act of asexual reproduction of 'Fismired' was accomplished when vegetative cuttings were taken from the initial selection in the spring of 2004 and grafted on rootstocks of the variety 'Maren,' in order to improve the branching ability. Cuttings from the successfully grafted stems were rooted in the summer of 2005, and cultivated for the first, small trial through the fall and winter of 2005.

Horticultural examination of plants grown from cuttings of the plant initiated in the summer of 2005 in Hillscheid, Germany, and continuing thereafter on a larger scale, has demonstrated that the combination of characteristics as herein disclosed for 'Fismired' are firmly fixed and are retained through successive generations of asexual reproduction.

'Fismired' has not been observed under all possible environmental conditions. The phenotype may vary significantly with variations in environment such as temperature, light intensity and day length Plant Breeders' Rights for this cultivar were applied for in the European Union on Apr. 10, 2008 and in Canada on Jul. 4, 2008. 'Fismired' has not been made publicly available more than one year prior to the filing of this application.

DESCRIPTION OF DRAWING

The accompanying photographic drawing shows typical flower and foliage characteristics of 'Fismired' with colors being as true as possible with an illustration of this type. The photographic drawing is a flowering pot, taken on Oct. 28, 2008, with plants from an early fall cultivation, potted in mid June, accordingly 19 weeks old.

DETAILED BOTANICAL DESCRIPTION

The measurements were taken in Hillscheid, Germany, latitude 50°, in mid December 2008 on about 20 week old plants growing in a greenhouse. Culture of these plants had started in late July 2008 with planting rooted cuttings in 14 cm pots and pinching about 2 weeks later. The plants were grown under natural day light in the fall (no black cloth to initiate earlier flowering) and at the moderately warm temperature of 18° C. for the bench heating.

Color Chart used: Royal Horticultural Society Colour Chart (R.H.S.) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this Poinsettia plant as a new and distinct variety.

1. Brilliant-red, distinctly lobed bracts
2. Relatively large inflorescences, well above the foliage canopy
3. Dark green foliage, oak-shaped leafs with pointed lobes
4. Small to medium sized habit with fairly upright directed branches 5. Relatively compact, dense, rounded plant habit
6. Early flowering response

DIFFERENCES BETWEEN THE NEW VARIETY 'FISMIRED' AND SIMILAR VARIETIES

'Fismired' has a similar bract color as 'Fisson' (U.S. Plant Pat. No. 9,365), but differs by having a somewhat weaker degree of lobing of bract and leaf margins, and more horizontally aspect of bracts, while bracts of 'Fisson' tend to slant somewhat downwards. Additionally, 'Fismired' has a more evenly mounding plant habit, tolerates lower temperatures during cultivation, and starts flowering more early.

'Fismired' differs from 'Fiselfi' (U.S. Plant Pat. No. 13,736) by having a slightly lighter overall flower color, longer bract shape, inflorescences borne higher above the foliage, somewhat more vigorous growth, and somewhat more upright habit than 'Fiselfi.'

Plant:

*Form, growth and habit.*—Low shrub, with the branches slanting upright, well-branching.
*Plant height* (*without pot*).—31.4 cm.
*Plant width.*—47.6 cm.
*Number of branches.*—8.8.
*Number of inflorescences.*—8.0.

Stem:

*Color of stem.*—Mainly RHS 147B, nearly no anthocyanin; light green, RHS 143C at the tip.
*Length of stem.*—Approximately 24–27 cm.
*Diameter.*—0.5–0.7 cm.
*Length of internodes.*—2–3.5 cm.
*Texture.*—Smooth, glabrous.

Foliage:

*Arrangement.*—Alternate.
*Quantity.*—6–8 leaves per branch.
*Aspect.*—Most petioles are horizontally to slightly upward directed, while the leaf blades show slightly downwards.
*Immature leaf color, upper surface.*—Approximately RHS 143A.
*Lower surface.*—RHS 144B.
*Mature, leaf color, upper surface.*—Dark green, RHS 139A.
*Lower surface.*—RHS 137B.
*Leaf length.*—13–16 cm.
*Leaf width.*—10.5–12.5 cm.
*Shape.*—Ovate with distinct lobbing, mostly pointed lobes
*Base shape.*—Obtuse, occasionally acute.
*Apex shape.*—Acuminate.
*Margin.*—Entire, lobes with rounded or acute tips.
*Texture.*—Flat, smooth, apart from the protruding veins on the under-side, glabrous.
*Color of veins, upper surface.*—Approximately RHS 53B at the base, fading towards the leaf tip.
*Color of veins, lower surface.*—RHS 145B to 145C.
*Petiole color, upper surface.*—Deep red, RHS 53A to purple, RHS 185A.
*Petiole color, lower surface.*—Dull purple, RHS 184B.
*Petiole length.*—5.0–6.5 cm.
*Diameter of petiole.*—2–3 mm.
*Texture upper and lower surfaces.*—Smooth, glabrous.

Inflorescence:

*Type.*—Terminal cyme with surrounding whorl of colored bracts.
*Flowering, botanically* (*opening of the stamina, shedding of pollen*).—In late November.
*Flowering, commercially* (*sufficiently colored bracts*).—Around November 15.
*Flowering response time.*—About 7.5–8 weeks from equinox.
*Duration of flowering.*—Depends on light and environment, at least 4–8 weeks of 'shelf' life.
*Fragrance.*—Absent.
*Shape of inflorescence.*—Rosette-like arrangement with the bracts overlapping, tight centre.
*Diameter of inflorescence.*—25–29 cm.
*Inflorescence, vertical diameter.*—2.0–3.5 cm.
*Number of completely colored bracts per inflorescence* (*sized over 2 cm*).—12–14.
*Single bract, shape.*—Ovate, moderate oak-leaf-shape.
*Bract, apex.*—Acuminate.
*Bract, base.*—Acute to obtuse.
*Single bract, length of blade.*—14.0–16.5 cm, younger bracts diminishing in size.
*Single bract, width of blade.*—9.5–11.5 cm.
*Bract color, upper side.*—Between RHS 45B and 45C.
*Bract color, lower side.*—RHS 46D.
*Vein color, upper surface.*—Indistinct, similar as bract blade.
*Vein color, lower surface.*—Pale pink to pink, RHS 49D to 54C.
*Texture.*—Smooth to somewhat rugose, glabrous.
*Bract petiole, length.*—About 2.0–2.5 cm, shorter with younger bracts.
*Bract petiole diameter.*—2–3 mm.
*Petiole color, upper surface.*—Red, RHS 53B.
*Petiole color, lower surface.*—Approximately RHS 159A, a few are RHS 51C.

Cyme (true inflorescence):

*Cyme, diameter.*—2.0–2.3 cm.
*Number of cyathia.*—Most often 7–10, borne in a tight cluster.
*Cyathium, shape.*—Ovate.
*Cyathium, diameter.*—0.4 cm.
*Cyathium, length.*—0.6–0.7 cm.
*Color.*—RHS 144A to 144B, top is RHS 46B.
*Peduncle length.*—3 mm.
*Peduncle color.*—RHS 144B to 144C.
*Nectar cups.*—One or two per cyathium.
*Nectur cup, width.*—Mostly 4 mm.
*Nectar cup, color.*—Yellow-orange, RHS 15A to 17A, reddish infusion may occur at the margin: RHS 33A to 33B, or 40B.

Reproductive organs:

*Stamen* (*actually reduced male florets*).—Usually in a small bunch of 15–20 at the top of the cyathium.
*Shape.*—Strap-like.
*Filament length.*—2–3 mm.
*Filament color.*—Red, RHS 46A to 46B.
*Anther color.*—Yellow, RHS 11A.
*Anther diameter.*—1 mm.
*Pollen quantity.*—Moderate (normal quantity).
*Pollen color.*—Yellow, RHS 12A.

Disease/pest resistance: Disease resistance or susceptibility has not been observed on this hybrid.

What is claimed is:

1. A new and distinct variety of Poinsettia plant named 'Fismired,' substantially as illustrated and described herein.

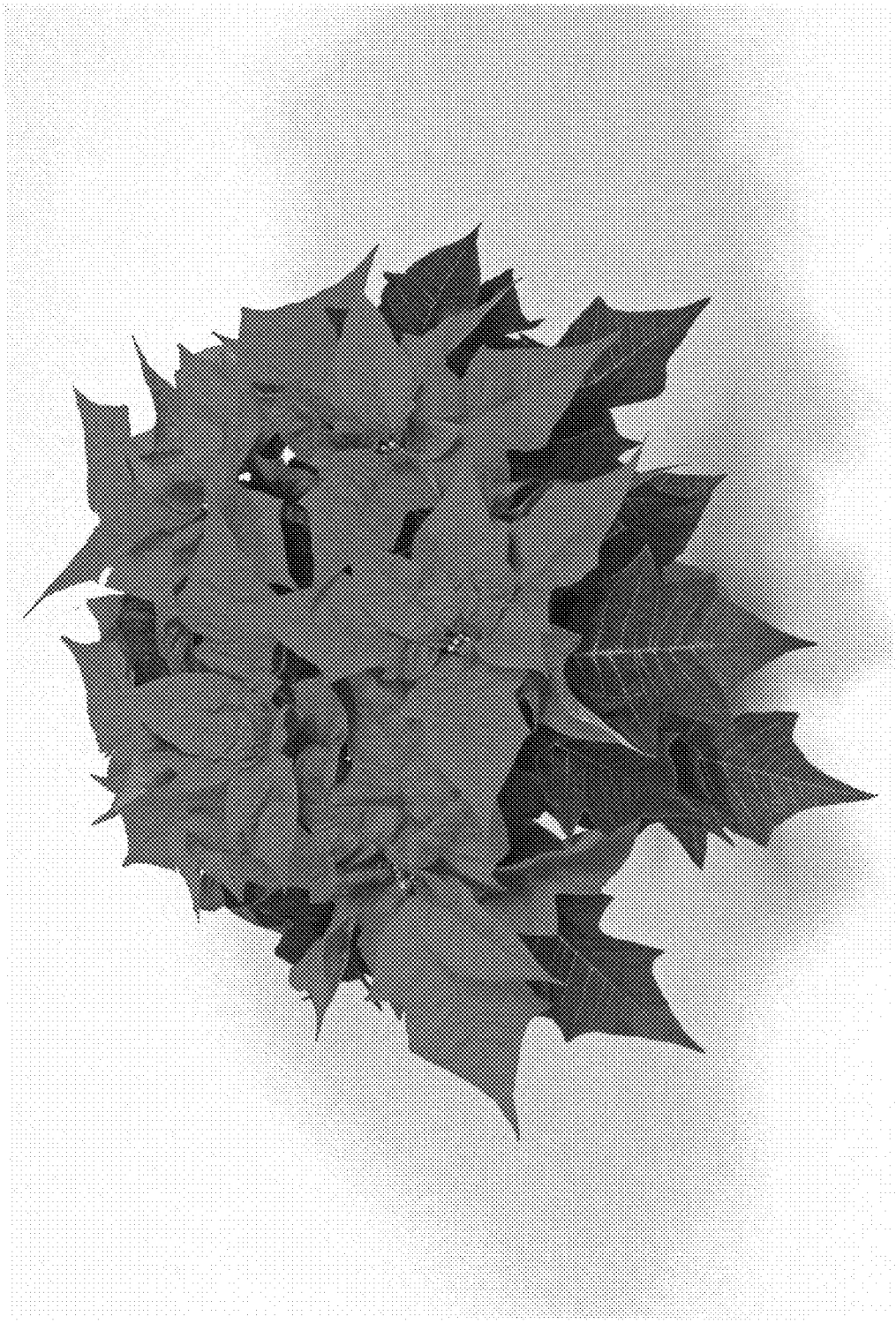

* * * * *